(12) United States Patent
Sugitani et al.

(10) Patent No.: US 11,980,371 B2
(45) Date of Patent: *May 14, 2024

(54) INDWELLING CLIP

(71) Applicant: ZEON CORPORATION, Tokyo (JP)

(72) Inventors: Tatsurou Sugitani, Tokyo (JP); Hikaru Mizuno, Tokyo (JP); Masakazu Ninomiya, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 621 days.

This patent is subject to a terminal disclaimer.

(21) Appl. No.: 17/043,506

(22) PCT Filed: Mar. 29, 2019

(86) PCT No.: PCT/JP2019/014281
§ 371 (c)(1),
(2) Date: Sep. 29, 2020

(87) PCT Pub. No.: WO2019/189864
PCT Pub. Date: Oct. 3, 2019

(65) Prior Publication Data
US 2021/0106335 A1  Apr. 15, 2021

(30) Foreign Application Priority Data
Mar. 30, 2018  (JP) ................................. 2018-069010

(51) Int. Cl.
*A61B 17/122*  (2006.01)
*A61B 90/00*  (2016.01)
(Continued)

(52) U.S. Cl.
CPC ............ *A61B 17/122* (2013.01); *A61B 90/39* (2016.02); *A61B 2017/12004* (2013.01); *A61B 17/1285* (2013.01); *A61B 2090/3941* (2016.02)

(58) Field of Classification Search
CPC ..... A61B 17/122; A61B 17/1227; A61B 90/39; A61B 2017/12004; A61B 2090/3941
See application file for complete search history.

(56) References Cited

U.S. PATENT DOCUMENTS 5,520,701 A * 5/1996 Lerch ................. A61B 17/1285
606/151
5,634,932 A * 6/1997 Schmidt ............... A61B 17/122
606/142
(Continued)

FOREIGN PATENT DOCUMENTS

CN  204121088 U  1/2015
JP  2005-218680 A  2/2004
(Continued)

OTHER PUBLICATIONS

International Search Report issued in application No. PCT/JP2019/014279, dated Jun. 18, 2019.
(Continued)

*Primary Examiner* — Ryan J. Severson
(74) *Attorney, Agent, or Firm* — Knobbe, Martens, Olson & Bear, LLP

(57) ABSTRACT

An indwelling clip includes a clip main body having a pair of arm plate portions that can be opened in a substantially V shape with an elastic force and claw portions formed on respective tip portions of the arm plate portions. The indwelling clip also includes a fastening ring attached to the arm plate portions so as to be movable along a longitudinal direction of the pair of arm plate portions and be able to close the pair of arm plate portions by moving in a direction of the claw portions. An outer surface of the claw portion is provided with a fluorescent body containing a fluorescent pigment emitting red or near infrared light by being irradiated with excitation light.

4 Claims, 18 Drawing Sheets

(51) Int. Cl.
*A61B 17/12* (2006.01)
*A61B 17/128* (2006.01)

(56) References Cited

U.S. PATENT DOCUMENTS

| | | | | |
|---|---|---|---|---|
| 7,164,360 B2* | 1/2007 | Schiebler | ............ | A61B 17/122 340/568.2 |
| 7,357,805 B2* | 4/2008 | Masuda | ............... | A61B 17/122 606/151 |
| 7,953,473 B2* | 5/2011 | Kaji | ....................... | A61B 90/39 600/562 |
| 8,688,195 B2* | 4/2014 | Sohn | ................. | A61B 17/1227 600/426 |
| 9,060,807 B2* | 6/2015 | Kaji | ....................... | A61B 90/39 |
| 10,039,607 B2* | 8/2018 | Heigl | ..................... | A61B 90/39 |
| 10,441,292 B2* | 10/2019 | Tsueda | ................. | A61B 17/083 |
| 10,646,228 B2* | 5/2020 | Hayashi | ............. | A61B 17/1285 |
| 10,702,354 B2* | 7/2020 | Wada | ...................... | A61B 90/39 |
| 2003/0180221 A1* | 9/2003 | Miwa | ................. | A61K 49/0021 548/219 |
| 2004/0032332 A1* | 2/2004 | Schiebler | ............... | A61B 17/82 340/568.2 |
| 2005/0182318 A1* | 8/2005 | Kaji | ......................... | A61B 5/06 600/424 |
| 2006/0259049 A1* | 11/2006 | Harada | ................ | A61B 17/122 606/151 |
| 2010/0331674 A1 | 12/2010 | Sohn et al. | | |
| 2011/0160577 A1* | 6/2011 | Kaji | ......................... | A61B 5/06 600/426 |
| 2011/0237942 A1* | 9/2011 | Zako | ................... | G01N 21/6456 600/431 |
| 2012/0143050 A1* | 6/2012 | Heigl | .................... | A61B 90/39 29/17.3 |
| 2013/0072945 A1* | 3/2013 | Terada | ............... | A61B 17/1227 606/157 |
| 2013/0072946 A1* | 3/2013 | Terada | ................. | A61B 17/122 606/157 |
| 2017/0281176 A1 | 10/2017 | Maekubo et al. | | |
| 2017/0303817 A1* | 10/2017 | Henary | ................... | A61F 13/15 |
| 2018/0333156 A1* | 11/2018 | Hayashi | ............. | A61B 17/1285 |
| 2021/0106335 A1* | 4/2021 | Sugitani | ................. | A61B 90/39 |
| 2021/0113210 A1* | 4/2021 | Sugitani | ................. | A61B 90/39 |
| 2022/0096088 A1* | 3/2022 | Sato | ..................... | A61B 17/122 |

FOREIGN PATENT DOCUMENTS

| | | |
|---|---|---|
| JP | 2011-005227 A | 1/2011 |
| JP | 2016-108501 A | 6/2016 |
| WO | WO 2015/182737 A1 | 12/2015 |

OTHER PUBLICATIONS

International Preliminary Report on Patentability issued in corresponding application No. PCT/JP2019/014281, dated Oct. 6, 2020.
Extended European Search Report issued in EP Application No. 19776397.2, dated Nov. 23, 2021.
Office Action issued in Chinese Application No. 201980018156.3, dated Nov. 11, 2023.

* cited by examiner

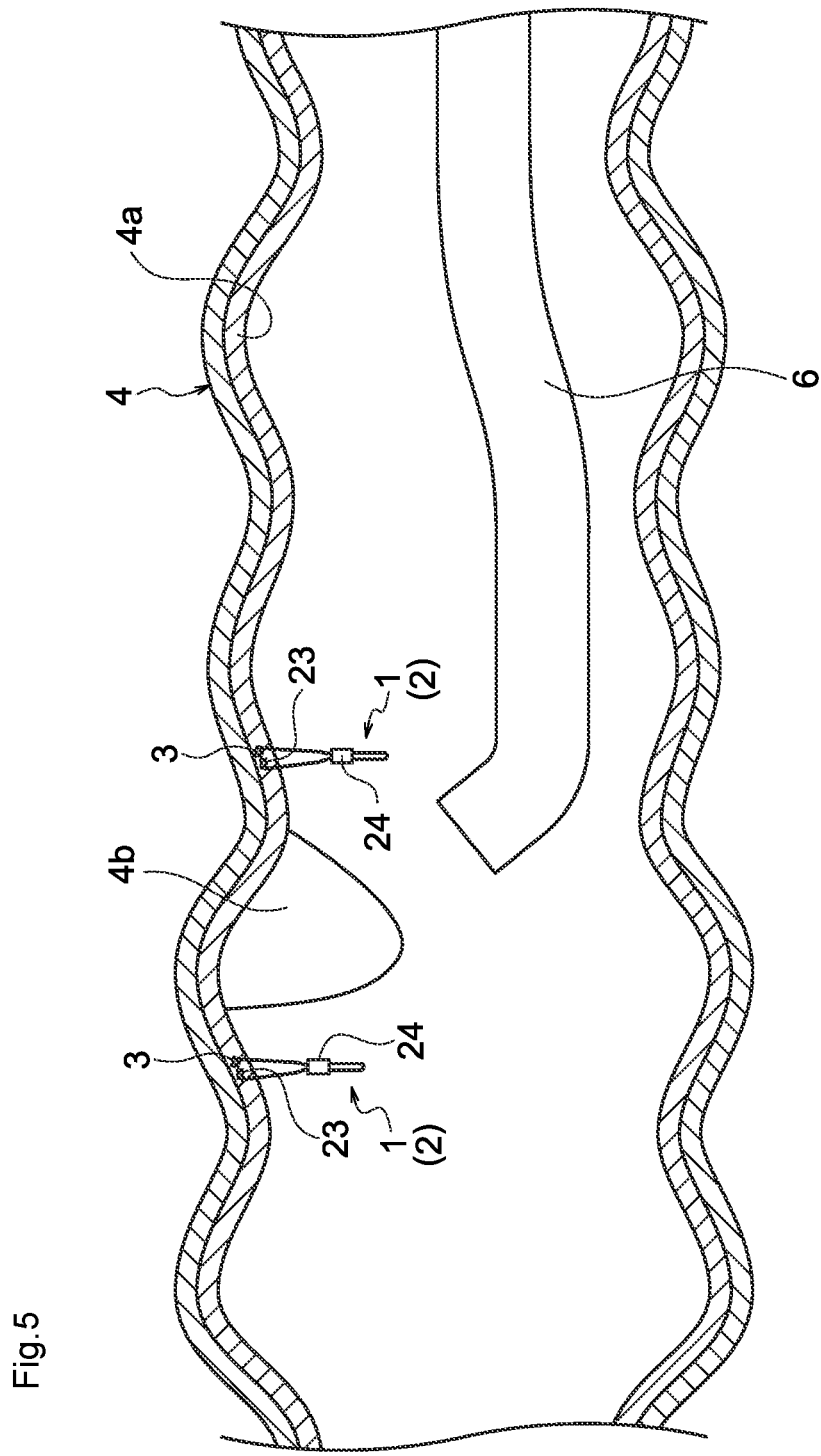

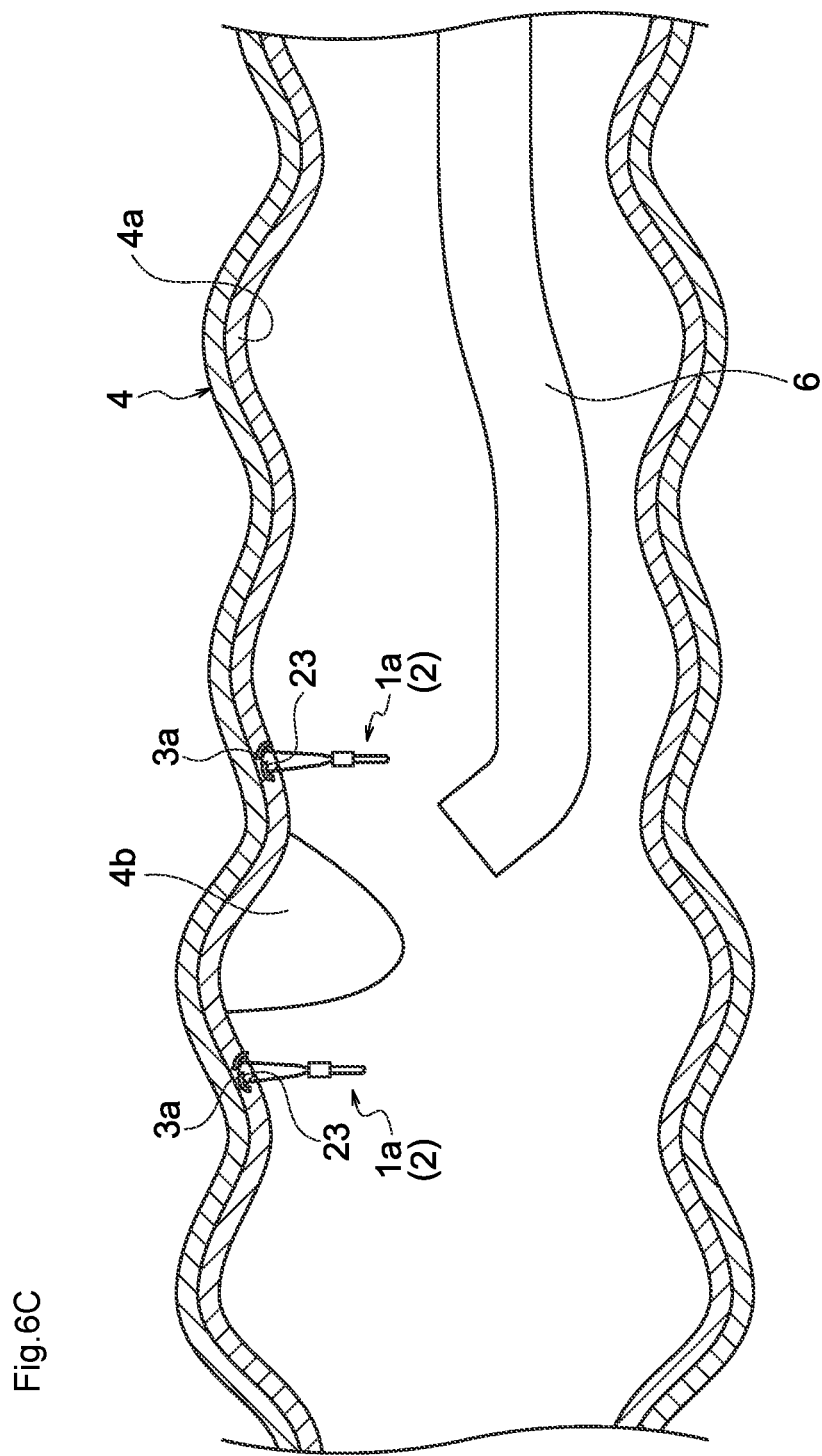

INDWELLING CLIP

TECHNICAL FIELD

The present invention relates to an indwelling clip usable as, for example, a marker that can be inserted into a lumen by means of an endoscope and whose position can be visually recognized from the outside of the lumen.

BACKGROUND ART

In general, diseases such as cancer of the digestive tract such as the esophagus, stomach, and large intestine develop and progress mainly from the mucous membrane of the digestive tract. Likewise, lung cancer develops mainly from the tracheal mucosa and bladder cancer develops and progresses mainly from the bladder mucosa. Accordingly, in order to confirm the diagnosis of a disease of a hollow organ such as the digestive tract, trachea, and bladder, it is essential to insert an endoscope into the hollow organ, observe the mucous membrane, and perform biopsy on the affected tissue. Then, the affected tissue is surgically excised as necessary based on the confirmed diagnosis.

However, a surgeon approaches the hollow organ from the outside during the surgical resection, and thus it is impossible to directly and visually recognize the affected area. In other words, in a case where the digestive tract, lungs, or bladder is observed with the naked eye or a laparoscope during thoracotomy, laparotomy, or laparoscopic surgery, the mucous membrane is invisible whereas the gastrointestinal serosa, tracheal serosa, and bladder peritoneal surfaces are visible. Accordingly, it is necessary to attach a marker into the hollow organ such that excision area determination is possible even in the case of observation from the outside of the hollow organ.

Surgical markers have been proposed as such a marker. The surgical markers are placed near a clip that is locked to a mucous membrane in the body and include an LED emitting near infrared light or an illuminant formed of a fluorescent luminescent substance (Patent Document 1).

However, the surgical marker that uses the LED as an illuminant requires electric power supply, and thus an increase in complexity arises in terms of device configuration and it is difficult to form the marker with compactness such that the marker can be passed through the treatment instrument guide tube of an endoscope. In addition, although the surgical marker that uses the illuminant formed of the fluorescent luminescent substance emits fluorescence by irradiation with excitation light from the outside of a hollow organ and it is not necessary to supply electric power for fluorescence emission, the intensity of the fluorescence emitted to the outside (serosal side) of the hollow organ is weak and it is practically difficult to visually recognize the luminous part from the outside of the hollow organ.

Patent Document 2 proposes a biological compression clip to address the above-described drawbacks of the surgical markers. The clip includes a clip main body having an arm portion and a tubular member fastened to the clip main body such that the arm portion can be closed. The clip is provided with a pressing portion that presses a mucous membrane (hollow organ inner wall) against the tubular member and contains a fluorescent pigment emitting red or near infrared light. In this clip, the pressing portion containing the fluorescent pigment is attached to the hollow organ inner wall with the wall of the hollow organ pressed, and thus fluorescence attenuation during transmission through the hollow organ wall (hemoglobin in blood in particular) is kept to a minimum. As a result, the luminous part can be visually and satisfactorily recognized even in the case of fluorescence observation from the outside of the hollow organ. However, in the clip illustrated in Patent Document 2, a resin material containing a fluorescent pigment constitutes the tubular member (fastening ring) for arm portion closing, and thus fastening to the hollow organ inner wall by the arm portion is likely to loosen and the attachment stability of the clip main body needs to be improved.

CITATION LIST

Patent Document

Patent Document 1: JP 2005-218680 A
Patent Document 2: WO 2015/182737 A

SUMMARY OF THE INVENTION

Problem to be Solved by the Invention

The invention has been made in view of such a point, and an object of the invention is to provide an indwelling clip that allows easy visual recognition of light emission of a fluorescent body from the outside of a hollow organ and that enables excellent attachment stability to the inner wall of the hollow organ.

Means for Solving Problem

An indwelling clip according to the invention includes a clip main body having:
  a pair of arm plate portions capable of opening in a substantially V shape with an elastic force;
  claw portions formed on respective tip portions of the arm plate portions; and
  a fastening ring attached to the arm plate portions so as to be movable along a longitudinal direction of the pair of arm plate portions and be able to close the pair of arm plate portions by moving in a direction of the claw portions,
  in which an outer surface of at least one of the claw portions is provided with a fluorescent body containing a fluorescent pigment emitting red or near infrared light by being irradiated with excitation light.

The indwelling clip of the invention is transported into a hollow organ and attached to the inner wall of the hollow organ by means of, for example, an endoscope and a clip device. When the clip is attached, the fluorescent body provided on the outer surface of the claw portion of the clip main body is pressed against the hollow organ inner wall.

As a result, according to the indwelling clip of the invention, fluorescence attenuation during transmission through a hollow organ wall is kept to a minimum and it is easy to visually recognize the light emission of the fluorescent body from the outside of the hollow organ. In addition, it is not necessary to configure the fastening ring closing the arm plate portion with a fluorescent body, and thus the design of the fastening ring is unrestricted and the clip is capable of being excellent in terms of the stability of attachment to the hollow organ inner wall. It should be noted that the visual recognition of the light emission of the fluorescent body from the outside of the hollow organ may be performed visually or by image recognition by means of an imaging device such as a laparoscope in accordance with the wavelength of the light or the like.

The fluorescent body may protrude from the claw portions to an outside of the arm plate portion. In addition, the fluorescent body may protrude outward from a tip of the claw portions. Further, the fluorescent body may be continuously provided from the outer surface of the claw portions to an outer surface of the arm plate portions. Further, the fastening ring may be made of metal.

BRIEF DESCRIPTION OF DRAWINGS

FIG. 5 is a diagram schematically illustrating a state where the clip of FIG. 1 is placed in a hollow organ;

FIG. 6C is a diagram schematically illustrating a state where the clip of FIG. 6A is placed in the body;

MODE(S) FOR CARRYING OUT THE INVENTION

Hereinafter, embodiments of the invention will be specifically described with reference to the drawings.

First Embodiment

Figure 1:
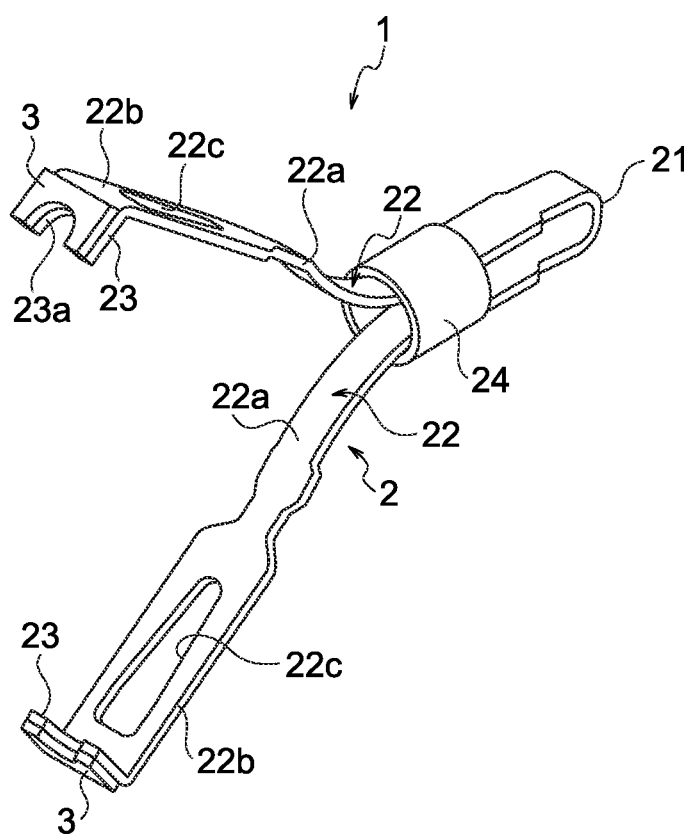
FIG. 1 is a perspective view illustrating an overall configuration of an indwelling clip of an embodiment of the invention in a state where an arm plate portion is open.

First, a first embodiment of the invention will be described with reference to FIGS. 1 to 5. As illustrated in FIG. 1, an indwelling clip 1 of the present embodiment is used as, for example, a marker that can be attached to the inner wall of a hollow organ in a living body and whose position can be visually recognized from the outside of the lumen. The indwelling clip 1 has a clip main body 2 and a fluorescent body 3.

The clip main body 2 includes a connecting plate portion 21, a pair of arm plate portions 22, and a fastening ring 24. The connecting plate portion 21 is folded in a substantially U shape. The arm plate portions 22 and 22 are integrally formed so as to be respectively continuous with the end portions of the U shape and open in a substantially V shape toward the tip side thereof.

Figure 2:
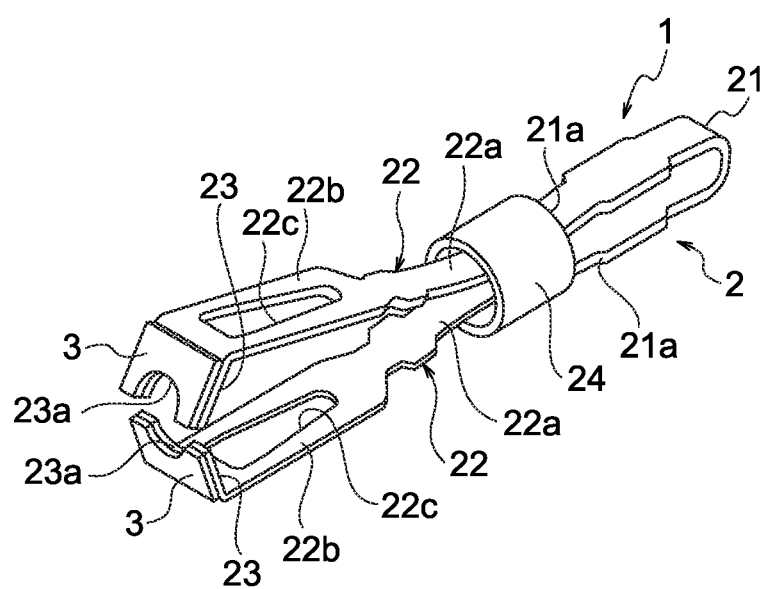
FIG. 2 is a perspective view illustrating a state where the arm plate portion of the clip of FIG. 1 is closed.

The fastening ring 24 is a ring-shaped member that is slidably and externally fitted onto the connecting plate portion 21 on the base end side of the arm plate portion 22. The fastening ring 24 is a member that is slid by means of a clip device 5 illustrated in FIG. 3A (described later). The clip device 5 has an inner sheath 52 and a connecting hook 51 disposed so as to be capable of moving forward and backward with respect to the inner sheath 52 and detachably connected to (disengageably engaged with) the connecting plate portion 21. The fastening ring 24 illustrated in FIGS. 1 and 2 is pressed by the distal end of the inner sheath 52, slides, and closes the arm plate portion 22 by the connecting hook 51 being pulled inward from the tip portion of the inner sheath 52 as illustrated in FIG. 4B with the connecting hook 51 illustrated in FIG. 3A connected to the connecting plate portion 21.

As illustrated in FIG. 1, a claw portion 23 is integrally formed in the tip portion of each arm plate portion 22. The claw portion 23 is folded toward the inner side (that is, in the closing direction) at the tip of the arm plate portion 22. Each claw portion 23 has a recessed notch portion 23a at the intermediate part of the tip thereof.

The connecting plate portion 21, the pair of arm plate portions 22, and the pair of claw portions 23 are formed by one thin and slender plate material being folded and molded. Although not particularly limited, the plate thickness of the plate material constituting the connecting plate portion 21, the pair of arm plate portions 22, and the pair of claw portions 23 is preferably 0.10 to 0.30 mm. An elastic metal plate is preferable as the plate material. For example, a stainless steel plate is used as the plate material. In addition, the fastening ring 24 is also made of metal in the present embodiment. The material of the fastening ring 24 is not particularly limited. The fastening ring 24 may be made of a metal (such as stainless steel) similar to the metal of the plate material constituting the arm plate portion 22 and so on. Alternatively, the fastening ring 24 may be made of a metal different from the metal of the plate material constituting the arm plate portion 22 and so on, examples of which include a titanium alloy, gold, and aluminum.

Each of the arm plate portions 22 has a base end portion 22a and a grip portion 22b. A through hole 22c is formed in the grip portion 22b of each arm plate portion 22. The through holes 22c are formed without impairing the desired strength of the arm plate portion 22 (grip portion 22b). The through holes 22c are formed from the viewpoint of elasticity (repulsive force) adjustment at a time when the arm plate portion 22 is closed by the fastening ring 24.

A substantially cylindrical ring member constitutes the fastening ring 24 slidably fitted on the connecting plate portion 21. Alternatively, the fastening ring 24 may be constituted by a spring obtained by a wire rod being wound into a coil shape. The connecting plate portion 21 is inserted through the guide hole inside the fastening ring 24, and the fastening ring 24 is mounted (externally fitted) so as to be axially movable (slideable) between the outer periphery of the connecting plate portion 21 and the outer periphery of the base end portion 22a of the arm plate portion 22. It should be noted that a stopper protrusion 21a is formed on the connecting plate portion 21 as illustrated in FIG. 2 such that the fastening ring 24 does not come off to the outside of the connecting plate portion 21.

In a state where the fastening ring 24 is disposed on the rear side of the arm plate portion 22 (connecting plate portion 21) as illustrated in FIG. 1, the arm plate portion 22 is open owing to the elasticity of the arm plate portion 22 itself. It should be noted that it is possible to close the arm plate portion 22, if necessary, by moving (sliding) the fastening ring 24 to a position near the tip of the base end portion 22a (close to the grip portion 22b) as illustrated in FIG. 2.

As illustrated in FIG. 1, the outer surface of at least one of the claw portions 23 is provided with the fluorescent body 3 containing a fluorescent pigment emitting red or near infrared light as a result of irradiation with excitation light. The pair of claw portions 23 are capable of meshing with each other. It is preferable that at least the fluorescent body 3 is mounted on the outer surface of the claw portion 23 that is positioned outside in a state where the claw portions 23 mesh with each other. The fluorescent body 3 is mounted onto the outer surface of the claw portion 23 by adhesion, insert molding, or the like.

Although the shape of the fluorescent body 3 in the present embodiment is the same as the outer surface shape of the claw portion 23, the shapes may be different from each other. It is preferable that the fluorescent body 3 is formed of a polymer material composition containing a fluorescent pigment. It is preferable that the fluorescent pigment emits fluorescence in a red or near infrared wavelength range of 600 to 1,400 nm. Light in such a wavelength range is highly transmissive with respect to human tissue such as skin, fat, and muscle and is capable of satisfactorily reaching approximately 5 mm to 20 mm below a biological tissue surface.

Examples of the fluorescent pigment that emits the fluorescence in the wavelength range described above include a water-soluble pigment such as riboflavin, thiamine, nicotinamide adenine dinucleotide (NADH), and indocyanine green (ICG) and an oil-soluble pigment such as the azoboron complex compound described in JP 2011-162445 A. A pigment highly compatible with a polymer material is particularly preferable in that the pigment is stably retained in the polymer material without elution in a living body. Especially, the azo-boron complex compound described in JP 2011-162445 A or the like is preferable in that the compound or the like is excellent in fluorescence emission intensity and in light resistance, heat resistance, and compatibility with respect to a polymer material such as polyurethane.

The preferred concentration of the fluorescent pigment in the polymer material composition containing the fluorescent pigment is usually and preferably 0.1 to 0.001% by mass although the concentration depends on the type of the polymer material used as a fluorescent pigment or a binder.

Usable as the polymer material containing the fluorescent pigment is polyurethane, polypropylene, polyethylene, polyvinyl chloride, polyamide, polyamide elastomer, or the like proportionally mixed with a curing agent as necessary.

The polymer material contains the fluorescent pigment by, for example, the fluorescent pigment being kneaded into the polymer material by means of a twin-screw kneader. Subsequently, the fluorescent body 3 can be obtained by extrusion or injection molding into a predetermined shape, during which post-processing is performed if necessary. The fluorescent body 3 is fixed to the outer surface of the claw portion 23 by means such as adhesion and insert molding.

It should be noted that a contrast agent such as barium sulfate may be added, if necessary, to the polymer material composition containing the fluorescent pigment. As a result, it is also possible to track the fluorescent body 3 in the hollow organ by imaging the fluorescent body 3 with an X-ray even if the indwelling clip 1 comes off the inner wall of the hollow organ after pinching of the inner wall of the hollow organ in the living body or the fluorescent body 3 falls from the clip main body 2.

In addition, the fluorescent body 3 may be a body in which the outer surface of the claw portion 23 of the clip main body 2 is coated with a paint containing a fluorescent pigment. In addition, the fluorescent body 3 may be a body in which the outer surface of a plate material formed of a polymer material composition containing a fluorescent pigment is turned into two layers or coated with a transparent material containing no fluorescent pigment. In addition, a fluorescent pigment may be fixed by means of gelatin or the like on the surface of a plate material formed of a material containing no fluorescent pigment. The thickness of the fluorescent body 3 is determined such that sufficient fluorescence characteristics can be obtained. Although not particularly limited, the thickness is preferably 1 to 5,000 m.

Figure 3A:
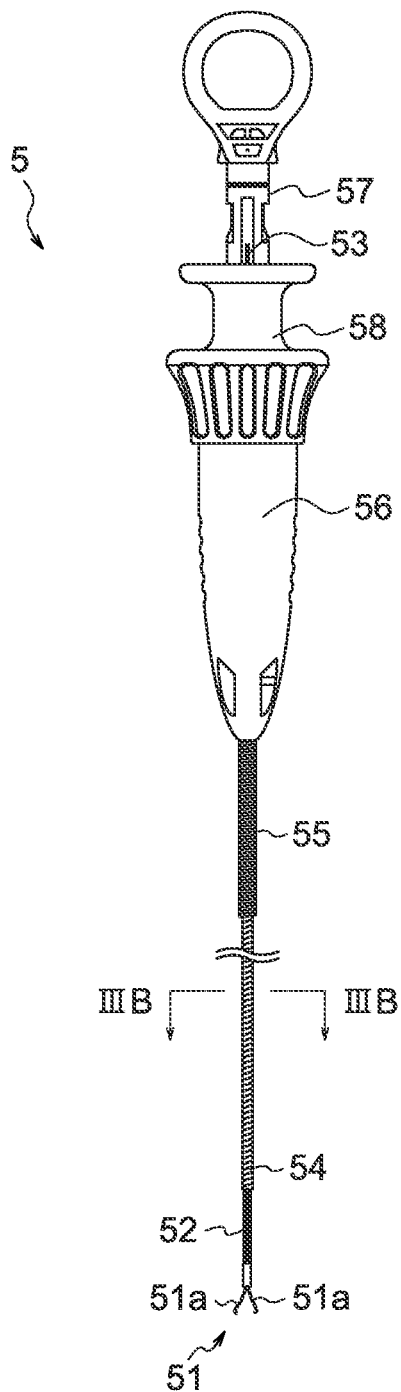
FIG. 3A is a diagram illustrating the appearance of a clip device of the embodiment of the invention.

In the present embodiment, the indwelling clip 1 is transported into a hollow organ 4 illustrated in FIG. 5 and the clip 1 is attached to a specific position on the inner wall of the hollow organ 4 by means of, for example, the endoscope that is illustrated in FIG. 5 and the clip device 5 illustrated in FIG. 3A. For example, the clip 1 is attached around a tumor 4b at a part of a mucous membrane (hollow organ inner wall) 4a on the inner wall of the hollow organ 4 so that the tumor is located. It is preferable that a plurality of the clips 1 are attached to the inner wall of the hollow organ 4 although both the single clip 1 and the plurality of clips 1 may be attached to the inner wall of the hollow organ 4.

Here, the clip device 5 illustrated in FIG. 3A will be described. The clip device 5 is to transport the indwelling clip 1 into the body via the treatment instrument guide tube of an endoscope 6 illustrated in FIG. 5 and perform internal tissue gripping and placement (clipping).

The clip device 5 has the connecting hook 51, the inner sheath 52, a drive wire 53, an outer sheath 54, a reinforcing coil 55, a first slider portion 56, a base portion 57, and a second slider portion 58.

Figure 3B:
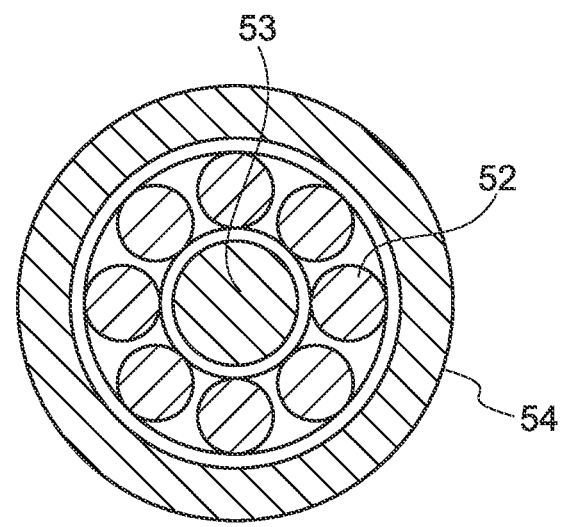
FIG. 3B is a cross-sectional view taken along line IIIB-IIIB in FIG. 3A.

As illustrated in FIG. 3B, the tubular inner sheath 52 is inserted through the tubular outer sheath 54 and the drive wire 53 is inserted through the inner sheath 52. The inner sheath 52 is slidable in the outer sheath 54, and the drive wire 53 is slidable in the inner sheath 52.

The outer sheath 54 is made of a flexible hollow tube, and a coil tube is used in the present embodiment. Usable as the coil tube is a flat wire coil tube obtained by spiral winding of a long flat plate made of metal (stainless steel) or the like. Alternatively, a round wire coil tube or an inner flat coil tube may be used. The inner diameter of the tip portion of the outer sheath 54 is approximately 2 to 3 mm.

The inner sheath 52 is made of a flexible hollow tube, and a wire tube is used in the present embodiment. The wire tube is a tube made of a hollow stranded wire obtained by a plurality of wires (cables) made of metal (stainless steel) or the like being spirally twisted so as to become hollow. It should be noted that the inner sheath 52 may be a sheath in which a wire tube is mainly used and only a part of the tip side thereof is a coil tube. The inner diameter of the tip portion of the inner sheath 52 is approximately 1.5 to 2.5 mm.

The drive wire 53 is made of a flexible wire, and a wire rope is used in the present embodiment. The wire rope is a rope made of a stranded wire obtained by spiral twisting of a plurality of wires (cables) made of metal (stainless steel) or the like. Alternatively, a wire tube similar to the inner sheath 52 may be used as the drive wire 53.

The connecting hook 51 disposed at the distal end of the clip device 5 illustrated in FIG. 3A has a pair of arm portions 51a and 51a made of an elastic body disposed in a substantially V shape toward the tip thereof. By cooperation with the inner sheath 52, the connecting hook 51 is capable of taking two, open and closed, states. Claw portions are formed by folding to the inner side (side of mutual facing) in the tip portions of the arm portions 51a and 51a of the connecting hook 51, and thus the connecting plate portion 21 of the clip main body 2 can be gripped and connected.

The base end portion of the connecting hook 51 is a U-shaped portion that is formed in a substantially U shape and continuous with the base end portions of the pair of arm portions 51a and 51a. The connecting hook 51 can be formed by one slender plate material made of an elastic body being appropriately folded (plastically deformed). Although not particularly limited, the plate material constituting the connecting hook 51 has a plate thickness of approximately 0.20 to 0.24 mm and a width of approximately 0.6 mm. Stainless steel or the like is used as the plate material.

The base end portion of the connecting hook 51 is fixed by laser welding or the like to the tip (distal end) of the drive wire 53 slidably inserted in the inner sheath 52. The connecting hook 51 may be swingable with respect to the drive wire 53 by a substantially annular ring member being fixed by laser welding or the like to the distal end of the drive wire 53 and the U-shaped portion of the connecting hook 51 being passed through the ring member.

The vicinity of the base end (proximal end) side of the outer sheath 54 is inserted in the reinforcing coil 55 and integrally fixed in the reinforcing coil 55. The reinforcing coil 55 is integrally fixed in the first slider portion 56, and the distal end side part of the base portion 57 is inserted and disposed inside the first slider portion 56. The first slider portion 56 is slidable with respect to the base portion 57 such that the first slider portion 56 can be positioned between a position at which the first slider portion 56 has moved to the tip (distal end) side and two positions at which the first slider portion 56 has moved to the base end portion (proximal end) side.

The second slider portion 58 is slidably held by the base portion 57. The inner sheath 52 is fixed to the base portion 57. The proximal end of the drive wire 53 is fixed to the second slider portion 58.

When the second slider portion 58 is slid to the tip side (distal end side) with respect to the base portion 57, the inner sheath 52 is pulled in with respect to the drive wire 53 and the connecting hook 51 at the tip of the drive wire 53 protrudes from the tip of the inner sheath 52 and opens owing to its own elasticity. When the second slider portion 58 is slid to the base end side (proximal end side) with respect to the base portion 57, the drive wire 53 is pulled in with respect to the inner sheath 52 and the connecting hook 51 at the tip of the drive wire 53 gradually closes while moving into the inner sheath 52 and is embedded into the inner sheath 52. As a result, the connecting hook 51 is completely closed.

When the first slider portion 56 is slid to the base end side position with respect to the base portion 57, the inner sheath 52 is capable of protruding from the tip of the outer sheath 54. Conversely, when the first slider portion 56 is slid to the tip side position with respect to the base portion 57, the tip of the inner sheath 52 can be stored (embedded) into the outer sheath 54.

Figure 4A:
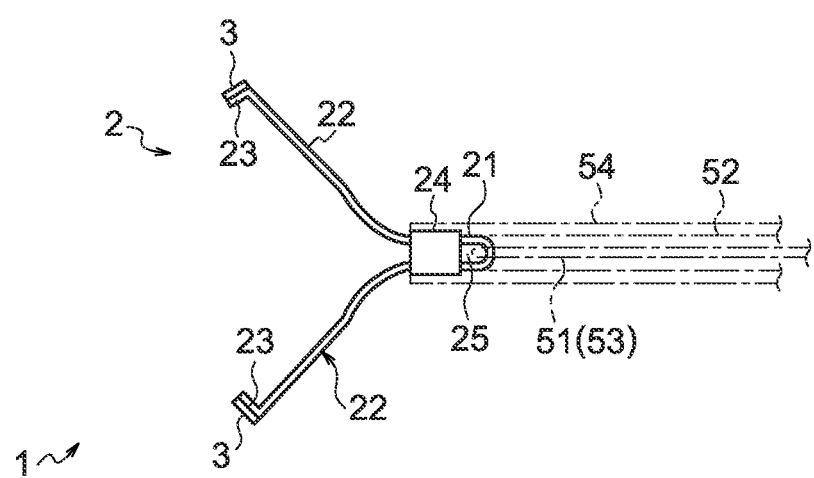
FIG. 4A is a diagram illustrating a state where the clip of FIG. 1 protrudes from the distal end of the clip device of FIG. 3A.
Figure 4B:
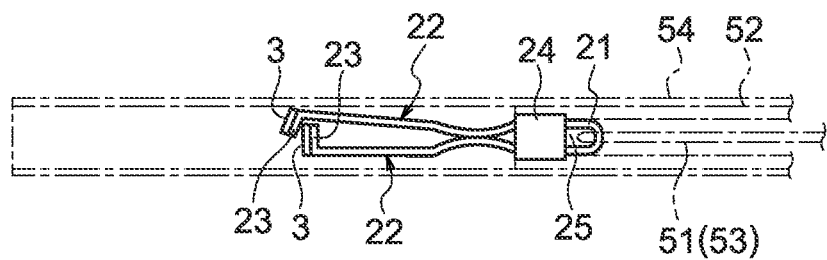
FIG. 4B is a diagram illustrating a state where the clip of FIG. 1 is accommodated in the distal end portion of the clip device of FIG. 3A.

Next, an example of how the indwelling clip 1 is used will be described with reference to FIGS. 4A, 4B, and 5. The connecting hook 51 of the clip device 5 is engaged with a connecting hole 25 formed inside the connecting plate portion 21 of the clip main body 2, and the connecting hook 51 is pulled into the inner sheath 52. As a result, the connecting hook 51 is closed and the clip main body 2 of the indwelling clip 1 is attached to the tip of the inner sheath 52 (see FIG. 4A).

In this state, the distal end portion of the inner sheath 52 to which the indwelling clip 1 (clip main body 2 and fluorescent body 3) is connected is pulled into the outer sheath 54 and the entire indwelling clip 1 is accommodated inside the distal end portion of the outer sheath 54 (see FIG. 4B). In this state, the fastening ring 24 of the clip main body 2 is positioned on the connecting plate portion 21 and the arm plate portion 22 is closed by the action of the inner wall of the outer sheath 54.

The distal end portion of the outer sheath 54 of the clip device 5 where the indwelling clip 1 is mounted is inserted into the hollow organ 4 by means of the endoscope 6 illustrated in FIG. 5. Next, the indwelling clip 1 is caused to protrude from the distal end of the outer sheath 54 by the outer sheath 54 illustrated in FIG. 3A being slid to the proximal end side. As a result, the arm plate portion 22 is opened owing to its own elasticity as illustrated in FIG. 4A.

Positioning around a lesion part such as the tumor 4b illustrated in FIG. 5 is performed with the arm plate portion 22 open. Next, the inner sheath 52 illustrated in FIG. 4A is slid to the distal end side with respect to the drive wire 53. Then, the fastening ring 24 slides to the tip side of the arm plate portion 22. As a result, the arm plate portions 22 are gradually closed (approach each other) and a part of the mucous membrane 4a is sandwiched.

The inner sheath 52 is further slid to the distal end side with respect to the drive wire 53, the fastening ring 24 is moved to the tip side of the arm plate portion 22, and the clip main body 2 of the indwelling clip 1 is completely closed. In this state, the inner sheath 52 is slid to the proximal end side with respect to the drive wire 53, the connecting hook 51 is pushed out of the distal end of the inner sheath 52 and opened, and the gripping (engagement) by the connecting hook 51 of the clip main body 2 is released. As a result, the clipping of a part of the mucous membrane 4a by the indwelling clip 1 is completed as illustrated in FIG. 5.

Next, once the clip device 5 is removed from the endoscope, another and separately prepared indwelling clip 1 is mounted onto the distal end portion of the clip device 5 (or a separately prepared clip device similar in configuration to the clip device 5). Next, the distal end portion of the clip device 5 where the separately prepared indwelling clip 1 is mounted is transported to the vicinity of a site positioned on the opposite side across the tumor 4b. Then, the clip 1 is capable of clipping a part of the mucous membrane 4a in a manner similar to what has been described above. In this manner, the plurality of clips 1 are capable of clipping the mucous membrane 4a positioned around the tumor 4b.

As described above, in the present embodiment, the indwelling clip 1 is transported into the hollow organ 4 and the clip 1 is attached to a specific position by means of, for example, the endoscope 6 illustrated in FIG. 5 and the clip device 5 illustrated in FIG. 3A. When the clip 1 is attached, the fluorescent body 3 provided on the outer surface of the claw portion 23 of the clip main body 2 bites into and is pressed against the mucous membrane 4a of the inner wall of the hollow organ 4. At the part where the fluorescent body 3 is pressed, it is possible to eliminate blood from a blood vessel by compressing the underlying vascular network of the mucous membrane 4a. As a result, when irradiation with excitation light is performed inward (toward the mucous membrane side) from the outer side (serosal side) of the hollow organ 4 during thoracotomy, laparotomy, or laparoscopic surgery, the excitation light is unlikely to be absorbed by the hemoglobin contained in the blood of the underlying vascular network of the mucous membrane and the excitation light easily reaches the fluorescent body 3 provided on the outer surface of the claw portion 23.

The fluorescent body 3 provided on the outer surface of the claw portion 23 contains the fluorescent pigment that emits red or near infrared light as a result of irradiation with excitation light. Accordingly, excitation light emitted from the outside of the hollow organ 4 is hardly absorbed by the hemoglobin and is efficiently absorbed by the fluorescent pigment of the fluorescent body 3. As a result, the fluorescence emitted from the fluorescent pigment of the fluorescent body 3 is also emitted to the outside of the hollow organ 4 while being hardly absorbed by the hemoglobin. Accordingly, the light emission of the fluorescent body 3 attached on the mucous membrane 4a of the hollow organ 4 can be visually and satisfactorily recognized from the outside of the hollow organ 4. In addition, since the fastening ring 24 is metallic, the fastening of the indwelling clip 1 is unlikely to loosen and the attachment stability of the clip 1 is also improved. It should be noted that the visual recognition of the light emission of the fluorescent body 3 from the outside of the hollow organ 4 may be performed by means for facilitating visual fluorescence recognition without being affected by the excitation light being selected in accordance with the wavelengths of the excitation light and the fluorescence. For example, the visual recognition may be performed visually or by image recognition by means of an imaging device such as a medical near infrared camera system and a laparoscope provided with a near infrared camera.

When the fluorescent body 3 emits light by the excitation light emitted from the outside of the hollow organ 4 during thoracotomy, laparotomy, or laparoscopic surgery, the light emitted by the fluorescent body 3 may be imaged visually, by means of an imaging device, or the like, the fluorescent body 3 can be located from the outside of the hollow organ 4, and the lesion part such as the tumor 4b can be located therefrom. Accordingly, it is possible to excise the hollow organ 4 corresponding to the tumor 4b from the outside by means of an ordinary scalpel, a high-frequency knife, or the like and the excision can be limited to the minimum required range. It should be noted that the clip 1 can be taken out of the body together with the excision of the tumor 4b.

Second Embodiment

Next, a second embodiment of the invention will be described with reference to FIGS. 6A to 6C. It should be noted that the description will focus on changes from the first embodiment described with reference to FIGS. 1 to 5.

Figure 6A:
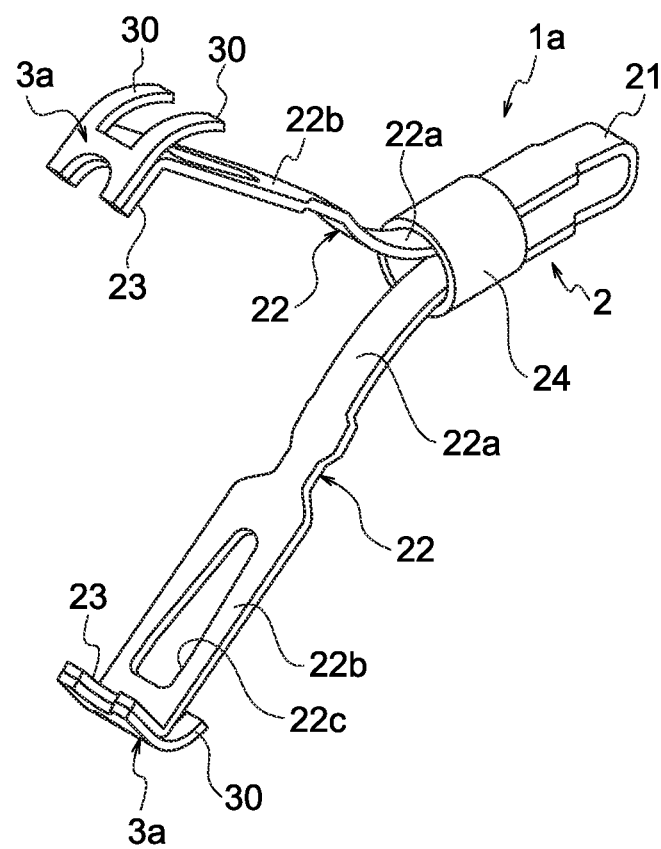
FIG. 6A is a perspective view illustrating an overall configuration of an indwelling clip of another embodiment of the invention in a state where an arm plate portion open.
Figure 6B:
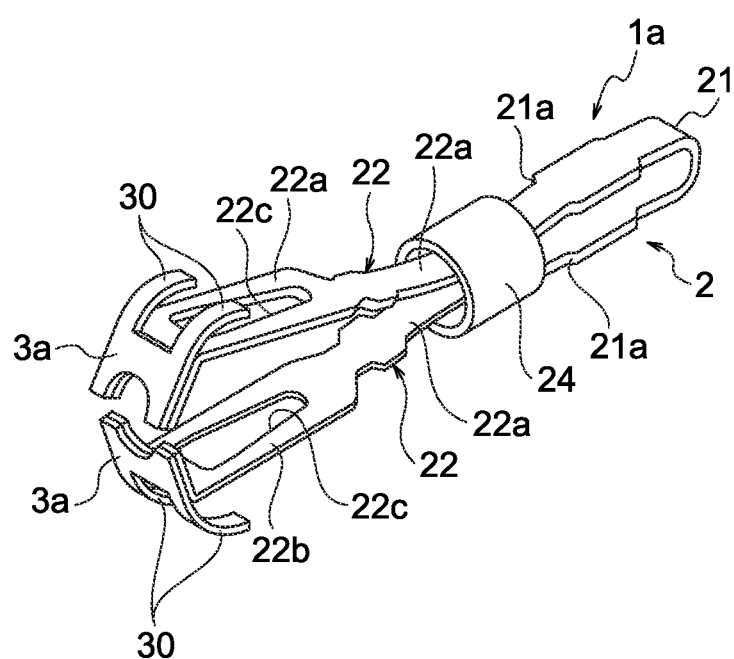
FIG. 6B is a perspective view illustrating a state where the arm plate portion of the clip of FIG. 6A is closed.

As illustrated in FIGS. 6A to 6C, an indwelling clip 1a of the present embodiment is similar to the indwelling clip 1 of the first embodiment except that a fluorescent body 3a is changed in shape and configuration. In other words, in the present embodiment, the clip main body 2 is similar to the clip main body 2 of the first embodiment and only the fluorescent body 3a is different from the fluorescent body 3 of the first embodiment. The fluorescent body 3a is formed integrally with a protruding portion 30 protruding from the claw portion 23 to the outside of the arm plate portion 22.

The protruding portion 30 is provided on each fluorescent body 3a and protrudes in a direction away from the clip main body 2 from the boundary between the claw portion 23 of the clip main body 2 and the arm plate portion 22 toward the outside of the arm plate portion 22 so as to extend the outer surface of the claw portion 23. The protruding portion 30 is formed integrally with the fluorescent body 3a and is made of, for example, a polymer material composition containing a fluorescent pigment.

Also in the present embodiment, the indwelling clip 1a is transported into the hollow organ 4 and the clip 1a is attached to a specific position by means of, for example, the endoscope 6 illustrated in FIG. 5 and the clip device 5 illustrated in FIG. 3A. When the clip 1a is attached, the tip portion of the claw portion 23 of the clip main body 2 bites into the mucous membrane 4a of the inner wall of the hollow organ 4 and the fluorescent body 3a provided on the outer surface of the claw portion 23 is pressed against the mucous membrane 4a. At the part where the fluorescent body 3a is pressed, it is possible to eliminate blood from a blood vessel by compressing the underlying vascular network of the mucous membrane 4a. As a result, when irradiation with excitation light is performed inward (toward the mucous membrane side) from the outer side (serosal side) of the hollow organ 4 during thoracotomy, laparotomy, or laparoscopic surgery, the excitation light is unlikely to be absorbed by the hemoglobin contained in the blood of the underlying vascular network of the mucous membrane and the excitation light easily reaches the fluorescent body 3a provided on the outer surface of the claw portion 23. In the present embodiment in particular, the area of the fluorescent body 3a is large and the fluorescent area is large owing to the presence of the protruding portion 30, and thus it is particularly easy to visually recognize the fluorescent light. Others are similar to those of the first embodiment described above.

Third Embodiment

Next, a third embodiment of the invention will be described with reference to FIG. 7. It should be noted that the description will focus on changes from the first embodiment described with reference to FIGS. 1 to 5.

Figure 7:
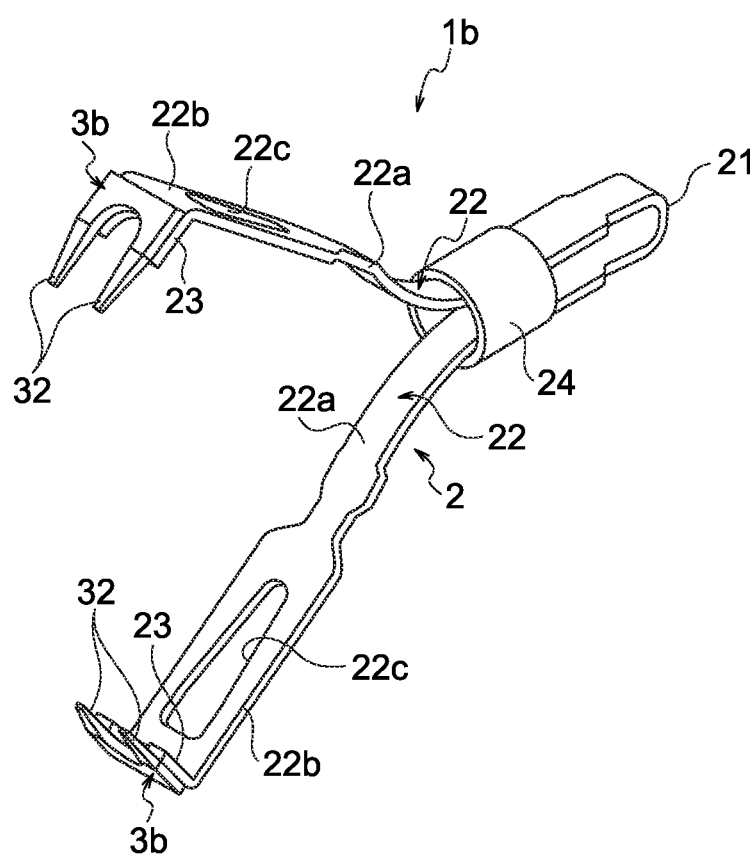
FIG. 7 is a perspective view illustrating an overall configuration of an indwelling clip of yet another embodiment of the invention in a state where an arm plate portion is open.

As illustrated in FIG. 7, an indwelling clip 1b of the present embodiment is similar to the indwelling clip 1 of the first embodiment except that a fluorescent body 3b is changed in shape and configuration. In other words, in the present embodiment, the clip main body 2 is similar to the clip main body 2 of the first embodiment and only the fluorescent body 3b is different from the fluorescent body 3 of the first embodiment. The fluorescent body 3b is formed integrally with a claw-shaped protruding portion 32 protruding from the claw portion 23 toward the tip of the claw portion 23.

The claw-shaped protruding portion 32 is provided on each fluorescent body 3b. The claw-shaped protruding portion 32 protrudes in a direction away from the claw portion 23 along the outer surface of the claw portion 23 from the tip of the claw portion 23 of the clip main body 2. The claw-shaped protruding portion 32 has a sharp tip. The claw-shaped protruding portion 32 is formed integrally with the fluorescent body 3b and is made of, for example, a polymer material composition containing a fluorescent pigment.

Also in the present embodiment, the indwelling clip 1b is transported into the hollow organ 4 and the clip 1b is attached to a specific position by means of, for example, the endoscope 6 illustrated in FIG. 5 and the clip device 5 illustrated in FIG. 3A. When the clip 1b is attached, the tip portion of the claw portion 23 of the clip main body 2 bites into the mucous membrane 4a of the inner wall of the hollow organ 4 together with the claw-shaped protruding portion 32 and the fluorescent body 3b provided on the outer surface of the claw portion 23 is pressed against the mucous membrane 4a. At the part where the fluorescent body 3b is pressed, it is possible to eliminate blood from a blood vessel by compressing the underlying vascular network of the mucous membrane 4a. As a result, when irradiation with excitation light is performed inward (toward the mucous membrane side) from the outer side (serosal side) of the hollow organ 4 during thoracotomy, laparotomy, or laparoscopic surgery, the excitation light is unlikely to be absorbed by the hemoglobin contained in the blood of the underlying vascular network of the mucous membrane and the excitation light easily reaches the fluorescent body 3b provided on the outer surface of the claw portion 23. In the present embodiment in particular, the area of the fluorescent body 3b is large and the fluorescent area is large owing to the presence of the claw-shaped protruding portion 32, and thus it is particularly easy to visually recognize the fluorescent light. Others are similar to those of the first embodiment described above.

Fourth Embodiment

Next, a fourth embodiment of the invention will be described with reference to FIG. 8. It should be noted that the description will focus on changes from the first embodiment described with reference to FIGS. 1 to 5.

Figure 8:
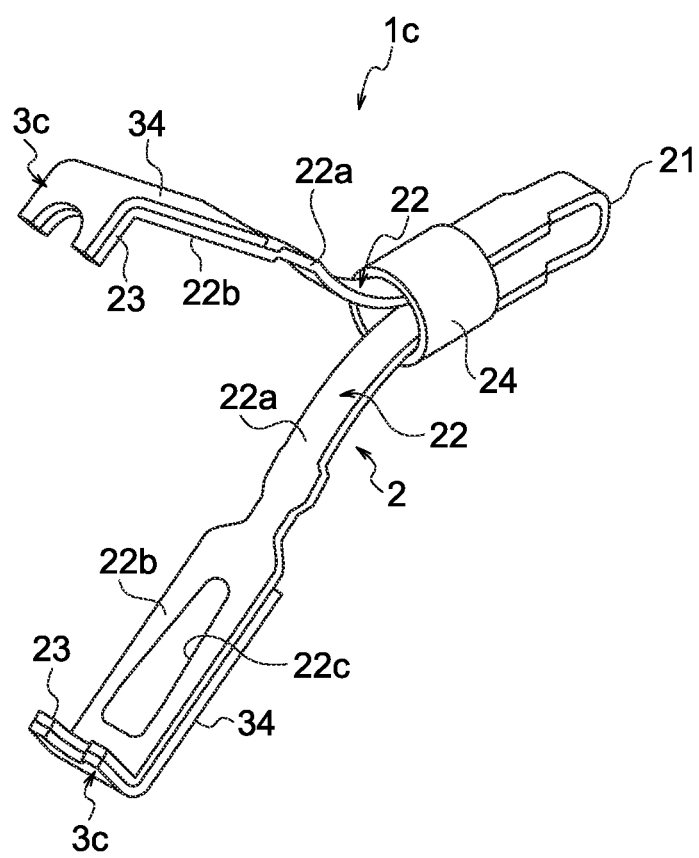
FIG. 8 is a perspective view illustrating an overall configuration of an indwelling clip of yet another embodiment of the invention in a state where an arm plate portion is open.

As illustrated in FIG. 8, an indwelling clip 1c of the present embodiment is similar to the indwelling clip 1 of the first embodiment except that a fluorescent body 3c is changed in shape and configuration. In other words, in the present embodiment, the clip main body 2 is similar to the clip main body 2 of the first embodiment and only the fluorescent body 3c is different from the fluorescent body 3 of the first embodiment. The fluorescent body 3c is formed integrally with an extending portion 34 continuously formed from the outer surface of the claw portion 23 to the outer surface of the arm plate portion 22.

The extending portion 34 is formed on each fluorescent body 3a. The extending portion 34 is continuously formed from the outer surface of the claw portion 23 to the outer surface of the grip portion 22b in the arm plate portion 22. A part of the inner surface of the extending portion 34 may enter the through hole 22c formed in the arm plate portion 22. The part of the extending portion 34 entering the through hole 22c is preferable in that the fluorescent body 3c is unlikely to fall from the clip main body 2. The extending portion 34 is formed integrally with the fluorescent body 3c and is made of, for example, a polymer material composition containing a fluorescent pigment. It should be noted that the extending portion 34 may also be formed inside the arm plate portion 22.

Also in the present embodiment, the indwelling clip 1c is transported into the hollow organ 4 and the clip 1c is attached to a specific position by means of, for example, the endoscope 6 illustrated in FIG. 5 and the clip device 5 illustrated in FIG. 3A. When the clip 1c is attached, the tip portion of the claw portion 23 of the clip main body 2 bites into the mucous membrane 4a of the inner wall of the hollow organ 4 together with the extending portion 34 and the fluorescent body 3c provided on the outer surface of the claw portion 23 is pressed against the mucous membrane 4a. At the part where the fluorescent body 3c is pressed, it is possible to eliminate blood from a blood vessel by compressing the underlying vascular network of the mucous membrane 4a. As a result, when irradiation with excitation light is performed inward (toward the mucous membrane side) from the outer side (serosal side) of the hollow organ 4 during thoracotomy, laparotomy, or laparoscopic surgery, the excitation light is unlikely to be absorbed by the hemoglobin contained in the blood of the underlying vascular network of the mucous membrane and the excitation light easily reaches the fluorescent body 3c provided on the outer surface of the claw portion 23. In the present embodiment in particular, the area of the fluorescent body 3c is large and the fluorescent area is large owing to the presence of the extending portion 34, and thus it is particularly easy to visually recognize the fluorescent light. Others are similar to those of the first embodiment described above.

Fifth Embodiment

Next, a fifth embodiment of the invention will be described with reference to FIGS. 9 to 11. It should be noted that the description will focus on changes from the fourth embodiment described with reference to FIG. 8.

Figure 9:
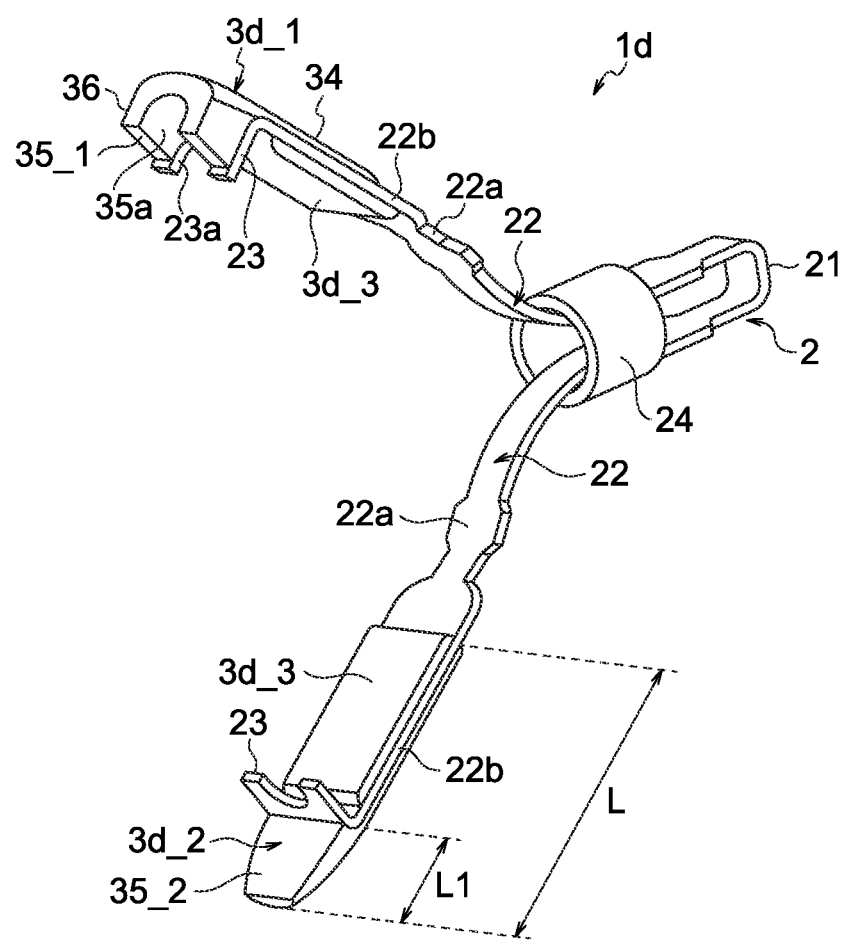
FIG. 9 is a perspective view illustrating an overall configuration of an indwelling clip of yet another embodiment of the invention in a state where an arm plate portion is open.

As illustrated in FIG. 9, an indwelling clip 1d of the present embodiment has a fluorescent body $3d\_1$. The fluorescent body $3d\_1$ is different from the fluorescent body 3c in the fourth embodiment in that the fluorescent body $3d\_1$ has a tip protruding portion $35\_1$. The fluorescent body $3d\_1$ is provided on the claw portion 23 formed in the tip portion of one arm plate portion 22 of the pair of arm plate portions 22 and 22. It should be noted that the indwelling clip 1d of the present embodiment is provided with fluorescent bodies $3d\_2$ and $3d\_3$ in addition to the fluorescent body $3d\_1$.

The fluorescent body $3d\_3$ is made of a flat plate-shaped fluorescent body. The fluorescent body $3d\_3$ is attached on the inner surface of each of the pair of arm plate portions 22 (grip portions 22b), and the grip portion 22b is sandwiched between the fluorescent body $3d\_3$ and the fluorescent body $3d\_1$ ($3d\_2$).

The fluorescent body $3d\_2$ is provided on the other arm plate portion 22 of the pair of arm plate portions 22 and 22. The fluorescent body $3d\_2$ provided on the other arm plate portion 22 is formed integrally with a tip protruding portion $35\_2$. The tip protruding portion $35\_2$ has a protrusion shape and protrudes from the tip portion of the arm plate portion 22 (grip portion 22b) to the outside of the tip of the arm plate portion 22.

The tip protruding portion $35\_2$ is made of a flat plate-shaped fluorescent body and is tapered in the width direction and the thickness direction toward the tip thereof. Accordingly, the tip protruding portion $35\_2$ has excellent piercing properties and the tip protruding portion $35\_2$ is capable of easily biting into the mucous membrane 4a of the inner wall of the hollow organ 4 with the clip 1d attached on the inner wall of the hollow organ 4.

The wall thickness of the tip protruding portion $35\_2$ is approximately equal to or larger than the wall thickness of the fluorescent body 3c illustrated in the fourth embodiment. Accordingly, the tip protruding portion $35\_2$ is given sufficient strength and the tip protruding portion $35\_2$ is capable of biting into the mucous membrane 4a of the inner wall of the hollow organ 4 without bending with the clip 1d attached on the inner wall of the hollow organ 4.

The tip protruding portion 35_2 protrudes along the longitudinal direction of the arm plate portion 22. The ratio L1/L of a protrusion length L1 from the tip portion of the arm plate portion 22 to a total length L of the fluorescent body 3d_2 is preferably 0.15 to 0.50. The same applies to the tip protruding portion 35_1 and the respective protrusion lengths of the tip protruding portion 35_1 and the tip protruding portion 35_2 are substantially equal to each other.

Figure 10:
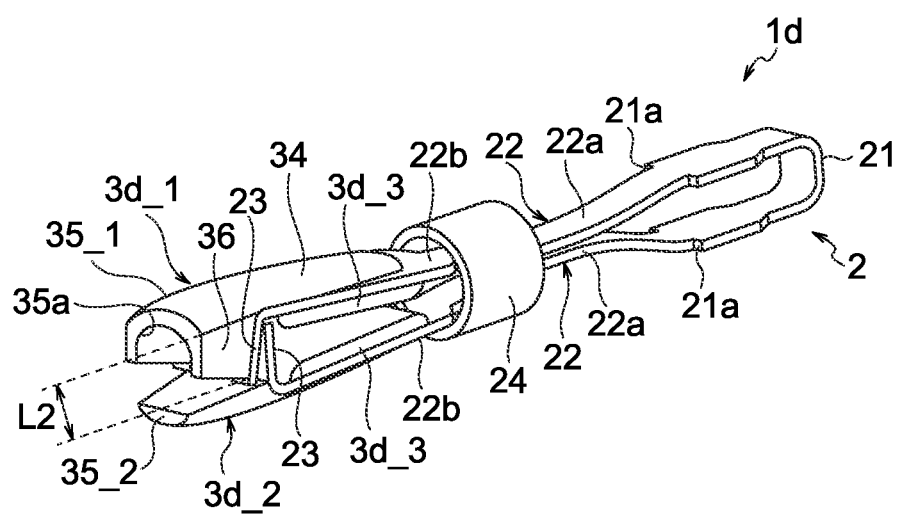
FIG. 10 is a perspective view illustrating a state where the arm plate portion of the clip of FIG. 9 is closed.
Figure 11:
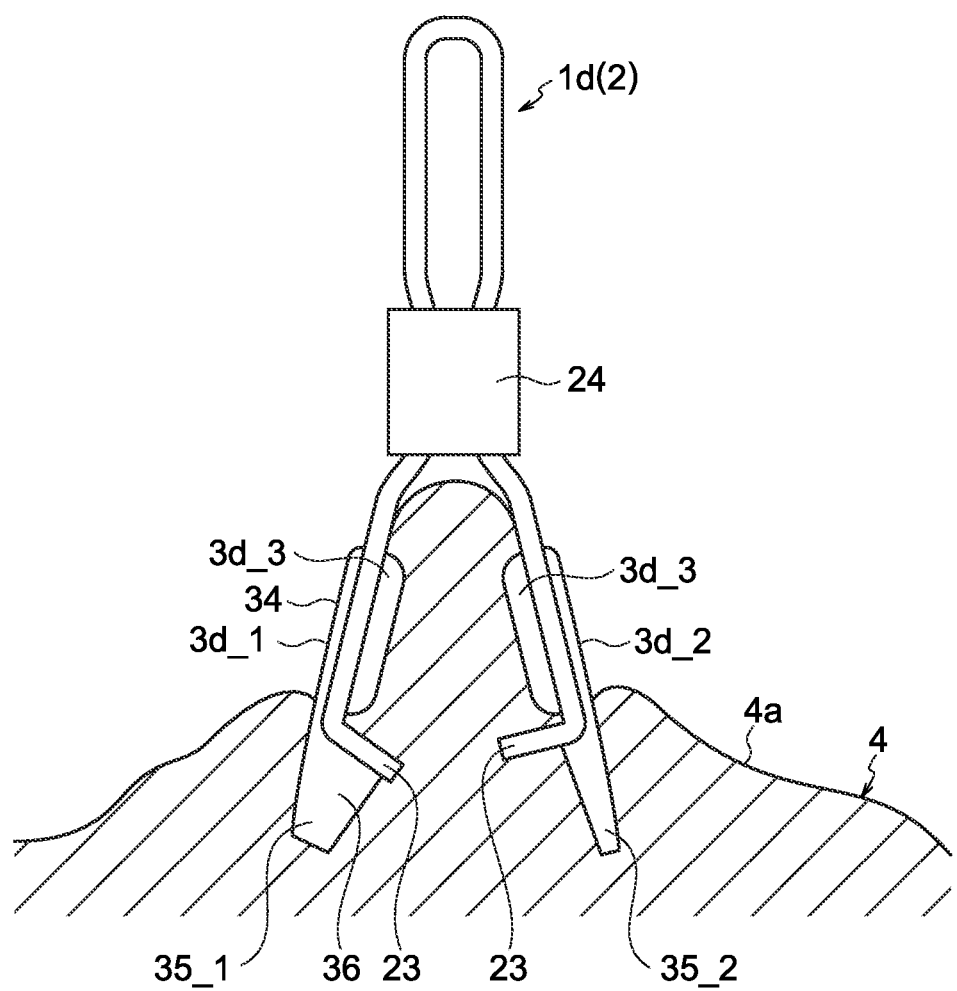
FIG. 11 is a diagram schematically illustrating a state where the clip of FIG. 9 is placed in a hollow organ.

As illustrated in FIG. 10, the fluorescent body 3d_1 is provided on the claw portion 23 that is disposed outside when the pair of arm plate portions 22 and 22 are closed. The fluorescent body 3d_1 provided on the claw portion 23 is formed integrally with the tip protruding portion 35_1. The tip protruding portion 35_1 has a protrusion shape and protrudes to the outside of the tip of the arm plate portion 22 from the outer surface of the claw portion 23 (or from the tip portion of the arm plate portion 22 (grip portion 22b)).

The shape of the tip protruding portion 35_1 corresponds to the shape of the outer surface of the claw portion 23, and a part (side portion 36) of the tip protruding portion 35_1 protrudes in the extension direction of the claw portion 23. Most of the claw portion 23 is covered with one end of the side portion 36 of the tip protruding portion 35_2.

A length L2 of the side portion 36 along the extension direction of the claw portion 23 is approximately equal to or shorter than the length of the claw portion 23 in the extension direction. Accordingly, the tip protruding portion 35_1 does not come into contact with the tip protruding portion 35_2 and the tip protruding portions 35_1 and 35_2 do not hinder the clipping by the clip 1d when the pair of arm plate portions 22 and 22 are closed.

In addition, the length L2 decreases toward the tip of the fluorescent body 3d_1 and the tip protruding portion 35_1 is tapered as a whole toward the tip thereof. Accordingly, the tip protruding portion 35_1 has excellent piercing properties and the tip protruding portion 35_1 is capable of easily biting into the mucous membrane 4a of the inner wall of the hollow organ 4 with the clip 1d attached on the inner wall of the hollow organ 4.

A recessed notch portion 35a is formed at the intermediate part of the tip of the tip protruding portion 35_1. Alternatively, the notch portion 35a may be omitted in a case where the notch portion 23a (see FIG. 9) is not formed in the claw portion 23.

The tip protruding portion 35_1 is curved (bent) along the width direction such that the shape (cross-sectional shape) of the tip protruding portion 35_1 is a substantially C shaped. In addition, a fluorescent body larger in volume (or area) than the tip protruding portion 35_2 constitutes the tip protruding portion 35_1. Accordingly, the fluorescence intensity of the tip protruding portion 35_1 exceeds the fluorescence intensity of the tip protruding portion 35_2.

The outer surfaces of the fluorescent bodies 3d_1 and 3d_2 are curved along the width direction of the fluorescent bodies 3d_1 and 3d_2 (similar to the width direction of the arm plate portion 22) from the viewpoint of easily accommodating the entire clip 1d inside the distal end portion of the outer sheath 54 of the clip device 5 (see FIG. 4B).

Also in the present embodiment, the indwelling clip 1d is transported into the hollow organ 4 and the clip 1d is attached to a specific position by means of, for example, the endoscope 6 illustrated in FIG. 5 and the clip device 5 illustrated in FIG. 3A. When the clip 1d is attached, the tip protruding portions 35_1 and 35_2 bite into the mucous membrane 4a of the inner wall of the hollow organ 4 together with the tip portion of the claw portion 23 of the clip main body 2 and the tip protruding portions 35_1 and 35_2 (tip-most portions of the tip protruding portions 35_1 and 35_2 in particular) are pressed against the mucous membrane 4a. At the parts where the tip protruding portions 35_1 and 35_2 are pressed, it is possible to eliminate blood from a blood vessel by compressing the underlying vascular network of the mucous membrane 4a. As a result, when irradiation with excitation light is performed inward (toward the mucous membrane side) from the outer side (serosal side) of the hollow organ 4 during thoracotomy, laparotomy, or laparoscopic surgery, the excitation light is unlikely to be absorbed by the hemoglobin contained in the blood of the underlying vascular network of the mucous membrane and the excitation light easily reaches the tip protruding portions 35_1 and 35_2 of the fluorescent bodies 3d_1 and 3d_2 and the fluorescent bodies 3d_1 and 3d_2 provided on the outer surface of the arm plate portions 22. In the present embodiment in particular, the area of the fluorescent body 3d_1 is large and the fluorescent area is large owing to the presence of the tip protruding portion 35_1, and thus it is particularly easy to visually recognize the fluorescent light. Others are similar to those of the fourth embodiment described above.

In addition, in the present embodiment, the pair of arm plate portions 22 and 22 are provided with the fluorescent bodies 3d_1 and 3d_2, respectively. Accordingly, when the mucous membrane 4a of the inner wall of the hollow organ 4 is bitten by the fluorescent body 3d_1 and the fluorescent body 3d_2 as illustrated in FIG. 11, it is possible to prevent the clip 1d from falling to one side of the pair of arm plate portions 22 and 22 and maintain a state where the clip 1d is erect substantially perpendicularly to the mucous membrane 4a.

Sixth Embodiment

Next, a sixth embodiment of the invention will be described with reference to FIGS. 12 to 14. It should be noted that the description will focus on changes from the fourth embodiment described with reference to FIG. 8.

Figure 12:
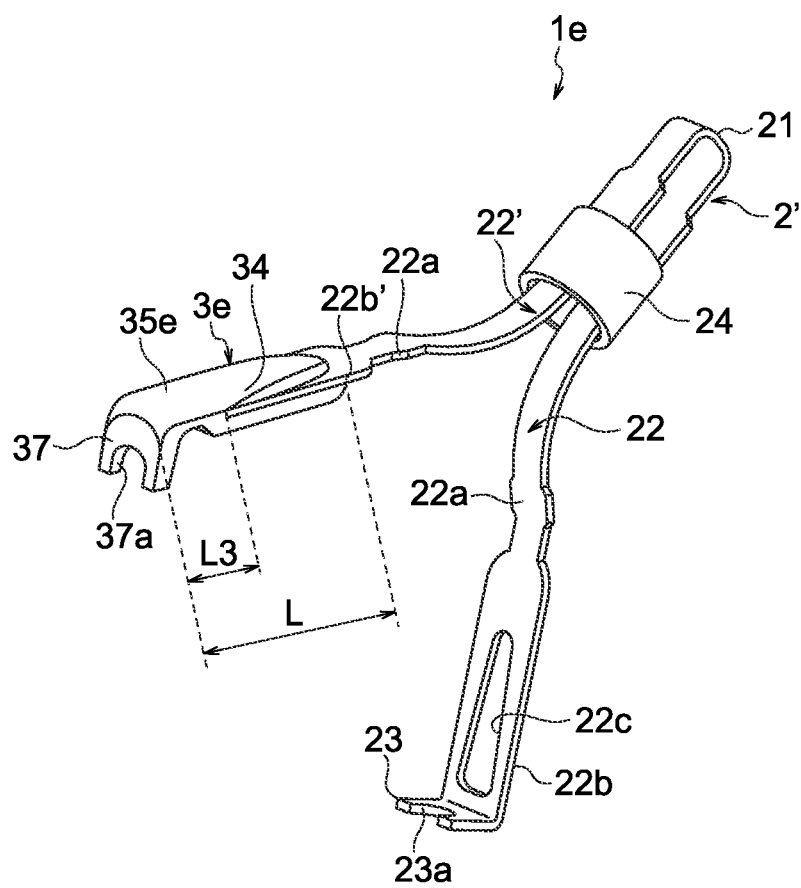
FIG. 12 is a perspective view illustrating an overall configuration of an indwelling clip of yet another embodiment of the invention in a state where an arm plate portion is open.
Figure 13:
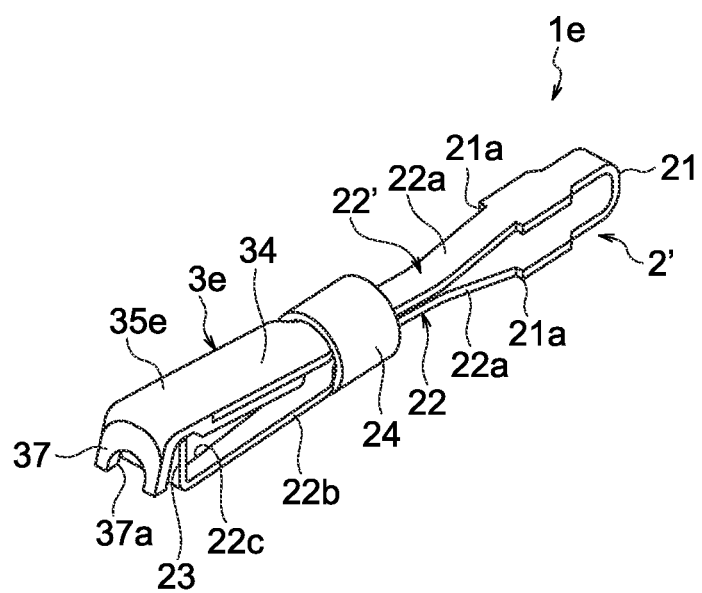
FIG. 13 is a perspective view illustrating a state where the arm plate portion of the clip of FIG. 12 is closed.

As illustrated in FIG. 12, an indwelling clip 1e of the present embodiment has a clip main body 2' and a fluorescent body 3e. The fluorescent body 3e is different from the fluorescent body 3c in the fourth embodiment in that the fluorescent body 3e has a tip protruding portion 35e. As illustrated in FIG. 14, the clip main body 2' has an arm plate portion 22' in addition to the arm plate portion 22.

The arm plate portion 22' differs from the arm plate portion 22b in that the arm plate portion 22' has a grip portion 22b'. A recessed notch portion 25 is formed at the intermediate part of the tip of the grip portion 22b', and the tip portion of the grip portion 22b' is not provided with the claw portion 23.

When the fluorescent body 3e is formed by injection molding or the like in the present embodiment, the grip portion 22b' of the arm plate portion 22' is integrated with the fluorescent body 3e by insert molding or the like. As illustrated in FIG. 12, the fluorescent body 3e has the tip protruding portion 35e. The tip protruding portion 35e differs from the tip protruding portion 35_2 illustrated in FIG. 9 in that the tip protruding portion 35e has a claw-shaped portion 37.

The tip protruding portion 35e protrudes from the tip portion of the arm plate portion 22' along the longitudinal direction of the arm plate portion 22'. The ratio L3/L of a protrusion length L3 of the tip protruding portion 35e to the total length L of the fluorescent body 3e is preferably 0.15 to 0.50.

The claw-shaped portion 37 is configured as a part of the tip protruding portion 35e and is formed integrally with the tip portion of the tip protruding portion 35e. As illustrated in FIG. 13, the claw-shaped portion 37 is disposed outside the claw portion 23 formed on one arm plate portion 22 when the pair of arm plate portions 22 and 22' are closed. It should be noted that the claw-shaped portion 37 may be configured as the entire tip protruding portion 35e.

The claw-shaped portion 37 is bent at a predetermined angle with respect to the extension direction of the tip protruding portion 35e and extends toward the inner side (that is, in the closing direction of the pair of arm plate portions 22 and 22'). The wall thickness of the claw-shaped portion 37 is approximately equal to or larger than the wall thickness of the fluorescent body 3c illustrated in the fourth embodiment. The claw-shaped portion 37 has a recessed notch portion 37a at the intermediate part of the tip thereof.

The claw-shaped portion 37 has a shape corresponding to the claw portion 23 formed in the tip portion of the arm plate portion 22 and is similar in role to the claw portion 23. In other words, in the present embodiment, the claw-shaped portion 37 replaces the claw portion 23 in one arm plate portion 22'. Accordingly, when the pair of arm plate portions 22 and 22' are closed, the claw portion 23 formed in the tip portion of the arm plate portion 22 and the claw-shaped portion 37 of the fluorescent body 3e provided on the arm plate portion 22' engage with each other and the mucous membrane 4a of the inner wall of the hollow organ 4 can be grabbed by means of the claw portion 23 and the claw-shaped portion 37.

As illustrated in FIG. 12, in the present embodiment, a part of the fluorescent body 3e is also provided on the inner surface of the arm plate portion 22' (grip portion 22b') and the outer surface and the inner surface of the grip portion 22b' are covered with the fluorescent body 3e. The part of the fluorescent body 3e that is formed on the inner surface of the grip portion 22b' is connected to the lower surface of the tip protruding portion 35e.

Figure 14:
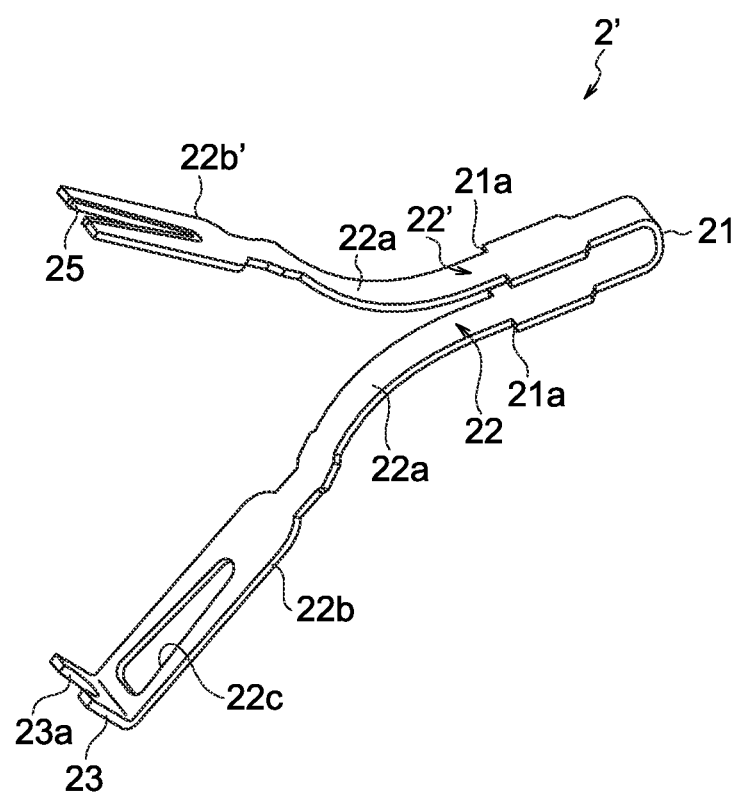
FIG. 14 is a perspective view illustrating an overall configuration of the clip main body that is illustrated in FIG. 12.

The fluorescent body 3e illustrated in FIG. 12 enters the notch portion 25 of the grip portion 22b' illustrated in FIG. 14. Accordingly, the fluorescent body 3e is firmly fixed to the grip portion 22b' and it is possible to prevent the fluorescent body 3e from falling (slipping) from the grip portion 22b'.

Also in the present embodiment, the indwelling clip 1e is transported into the hollow organ 4 and the clip 1e is attached to a specific position by means of, for example, the endoscope 6 illustrated in FIG. 5 and the clip device 5 illustrated in FIG. 3A. When the clip 1e is attached, the tip portion of the claw portion 23 of the clip main body 2' and the claw-shaped portion 37 of the fluorescent body 3e bite into the mucous membrane 4a of the inner wall of the hollow organ 4 and the tip protruding portion 35e (claw-shaped portion 37 of the tip protruding portion 35e in particular) is pressed against the mucous membrane 4a. At the part where the tip protruding portion 35e is pressed, it is possible to eliminate blood from a blood vessel by compressing the underlying vascular network of the mucous membrane 4a. As a result, when irradiation with excitation light is performed inward (toward the mucous membrane side) from the outer side (serosal side) of the hollow organ 4 during thoracotomy, laparotomy, or laparoscopic surgery, the excitation light is unlikely to be absorbed by the hemoglobin contained in the blood of the underlying vascular network of the mucous membrane and the excitation light easily reaches the tip protruding portion 35e of the fluorescent body 3e. In the present embodiment in particular, the area of the fluorescent body 3e is large and the fluorescent area is large owing to the presence of the claw-shaped portion 37, and thus it is particularly easy to visually recognize the fluorescent light. Others are similar to those of the fourth embodiment described above.

In addition, in the present embodiment, it is possible to increase the degree of freedom in designing the fluorescent body 3e and the clip main body 2' (grip portion 22b' in particular) by forming the fluorescent body 3e by injection molding or the like, examples of which include a part of the tip protruding portion 35e constituting the claw-shaped portion 37 and introducing a shape (notch portion 25) that has an anti-slip effect into the grip portion 22b'.

It should be noted that the invention is not limited to the above-described embodiments and the invention can be modified in various ways. For example, each element disclosed in the above-described embodiments can be modified in various ways and combined. In addition, the biological tissue in which the indwelling clips of the above-described embodiments are used is not particularly limited. Examples of the biological tissue include hollow organs such as the digestive tract, trachea, bladder, bile duct, pancreatic duct, ureter, renal tract, liver, kidney, and lung. In addition, the indwelling clip of the invention can also be used for applications other than partial hollow organ excision.

In the sixth embodiment, the fluorescent body 3e is integrated with the grip portion 22b' of the arm plate portion 22' by insert molding. Alternatively, the fluorescent body 3e may be fixed to the grip portion 22b' by means such as adhesion. In the sixth embodiment, the fluorescent body may be engaged with the through hole 22c formed in the arm plate portion 22. In this case, the through hole 22c may be partially covered with the fluorescent body. For example, only the vicinity of the peripheral edge of the through hole 22c may be covered with the fluorescent body.

In the sixth embodiment, the shape of the grip portion 22b' of the arm plate portion 22' is not particularly limited and may be appropriately changed. For example, the notch portion 25 may be formed in the grip portion 22b' such that the width thereof decreases toward the tip side of the grip portion 22b'.

EXPLANATIONS OF LETTERS OR NUMERALS 1, 1a, 1b, 1c, 1d, 1e INDWELLING CLIP
2, 2' CLIP MAIN BODY
21 CONNECTING PLATE PORTION
21a STOPPER PROTRUSION
22, 22' ARM PLATE PORTION
22a BASE END PORTION
22b, 22b' GRIP PORTION
22c THROUGH HOLE
23 CLAW PORTION
23a NOTCH PORTION
24 FASTENING RING
25 NOTCH PORTION
3, 3a, 3b, 3c, 3d_1, 3d_2, 3d_3, 3e FLUORESCENT BODY
30 PROTRUDING PORTION
32 CLAW-SHAPED PROTRUDING PORTION
34 EXTENDING PORTION
35_1, 35_2, 35e TIP PROTRUDING PORTION
35a NOTCH PORTION
36 SIDE PORTION

37 CLAW-SHAPED PORTION
37a NOTCH PORTION
4 HOLLOW ORGAN
4a MUCOUS MEMBRANE
4b TUMOR
5 CLIP DEVICE
51 CONNECTING HOOK
51a ARM PORTION
52 INNER SHEATH
53 DRIVE WIRE
54 OUTER SHEATH
55 REINFORCING COIL
56 FIRST SLIDER PORTION
57 BASE PORTION
58 SECOND SLIDER PORTION
6 ENDOSCOPE

What is claimed is:

1. An indwelling clip comprising a clip main body including:
   a pair of arm plate portions configured to be opened in a substantially V shape with an elastic force;
   claw portions formed on respective tip portions of the arm plate portions; and
   a fastening ring attached to the arm plate portions so as to be movable along a longitudinal direction of the pair of arm plate portions and be able to close the pair of arm plate portions by moving in a direction of the claw portions,
   wherein an outer surface of at least one of the claw portions is provided with a fluorescent body containing a fluorescent pigment emitting red or near infrared light by being irradiated with excitation light, and
   wherein the fluorescent body protrudes from the at least one of the claw portions in a direction toward a tip side in the longitudinal direction of the arm plate portions, and a protrusion length of the fluorescent body from a tip portion of the arm plate portion is greater than the thickness of the claw portion.

2. The indwelling clip according to claim 1, wherein the fluorescent body protrudes from the claw portions to an outside of the arm plate portions.

3. The indwelling clip according to claim 1, wherein the fluorescent body is continuously provided from the outer surface of the claw portions to an outer surface of the arm plate portions.

4. The indwelling clip according to claim 1, wherein the fastening ring is made of metal.

* * * * *

UNITED STATES PATENT AND TRADEMARK OFFICE
CERTIFICATE OF CORRECTION

| | |
|---|---|
| PATENT NO. | : 11,980,371 B2 |
| APPLICATION NO. | : 17/043506 |
| DATED | : May 14, 2024 |
| INVENTOR(S) | : Tatsurou Sugitani et al. |

It is certified that error appears in the above-identified patent and that said Letters Patent is hereby corrected as shown below:

In the Specification

In Column 6, Line 27, delete "5,000 m." and insert --5,000 µm.--.

In Column 16, Lines 33-38, delete "In the sixth embodiment, the fluorescent body may be engaged with the through hole 22c formed in the arm plate portion 22. In this case, the through hole 22c may be partially covered with the fluorescent body. For example, only the vicinity of the peripheral edge of the through hole 22c may be covered with the fluorescent body." and insert the same on Line 34 as a new paragraph.

Signed and Sealed this
Nineteenth Day of November, 2024

Katherine Kelly Vidal
*Director of the United States Patent and Trademark Office*